(12) United States Patent
Lee

(10) Patent No.: US 9,999,407 B2
(45) Date of Patent: Jun. 19, 2018

(54) TISSUE SAMPLING DEVICE

(76) Inventor: Choon Kee Lee, Denver, CO (US)

( * ) Notice: Subject to any disclaimer, the term of this patent is extended or adjusted under 35 U.S.C. 154(b) by 1843 days.

(21) Appl. No.: 13/355,500

(22) Filed: Jan. 21, 2012

(65) Prior Publication Data

US 2013/0190649 A1    Jul. 25, 2013

(51) Int. Cl.
*A61B 10/00* (2006.01)
*A61B 10/04* (2006.01)
*A61B 10/06* (2006.01)

(52) U.S. Cl.
CPC .............. *A61B 10/04* (2013.01); *A61B 10/06* (2013.01)

(58) Field of Classification Search
CPC ..... A61B 10/0266; A61B 10/04; A61B 10/06; A61B 10/0275; A61B 2017/3488; A61B 17/32056; A61B 2010/0225; A61B 2017/00349
USPC .................................................. 600/565–568
See application file for complete search history.

(56) References Cited

U.S. PATENT DOCUMENTS

| | | | |
|---|---|---|---|
| 5,562,102 A | 10/1996 | Taylor |
| 5,746,216 A | 5/1998 | Turturro |
| 5,762,069 A | 6/1998 | Kelleher |
| 5,779,648 A | 7/1998 | Banik |
| 5,782,747 A | 7/1998 | Zimmon |
| 5,810,744 A | 9/1998 | Chu |
| 5,823,971 A | 10/1998 | Robinson |
| 5,840,044 A | 11/1998 | Dassa |
| 5,961,534 A | 10/1999 | Banik |
| 6,019,758 A | 2/2000 | Slater |
| 6,053,877 A | 4/2000 | Banik |
| 6,071,248 A | 6/2000 | Zimmon |
| 6,083,150 A | 7/2000 | Aznoian |
| 6,110,127 A | 8/2000 | Suzuki |
| 6,139,508 A | 10/2000 | Simpson |
| 6,142,957 A | 11/2000 | Diamond |
| 6,322,522 B1 | 11/2001 | Zimmon |
| 6,419,640 B1 | 7/2002 | Taylor |
| 6,530,891 B2 | 3/2003 | Miller |
| 6,632,182 B1 | 10/2003 | Treat |
| 7,278,971 B2 | 10/2007 | Reydel |
| 7,794,409 B2 | 9/2010 | Damarati |
| 7,846,107 B2 | 12/2010 | Hoffman |
| 7,909,850 B2 | 3/2011 | Paternuosto |
| 2005/0165329 A1 | 7/2005 | Taylor |
| 2006/0089563 A1 | 4/2006 | McAlister |
| 2008/0300506 A1 | 12/2008 | McIntyre |
| 2008/0306406 A1 | 12/2008 | Thompson |

(Continued)

*Primary Examiner* — Jeffrey G Hoekstra
*Assistant Examiner* — Jonathan M Foreman

(57) ABSTRACT

Provided herein are a device and methods to obtain multiple serial samples from biologic tissues located in a tubular or cavitary space of a body. The device has a proximal and distal end, with a linear shaft connecting both ends. The distal end of the device comprises a tissue cutting assembly, a sample transport assembly and a sample storage assembly. The sample transport assembly comprises a slidable sample transport unit, a semi-cylindrical tubular sample chamber with a pair of axially linear rails located on both sides of said chamber and a system of differential pull wires. The sample transport unit slides on the rails of the sample chamber, providing longitudinally axial movement of the cup connected to said sample transport unit. The sample storage assembly comprises said sample chamber, a reversibly detachable sample catcher inserted in said sample chamber, a tubular sample housing and an expandable tubular sample housing.

8 Claims, 16 Drawing Sheets

(56) References Cited

U.S. PATENT DOCUMENTS

| | | |
|---|---|---|
| 2008/0319341 A1 | 12/2008 | Taylor |
| 2009/0227893 A1 | 9/2009 | Coonahan |
| 2009/0299217 A1 | 12/2009 | Bleibach |
| 2010/0094166 A1 | 4/2010 | Kraemer |
| 2010/0204610 A1 | 8/2010 | Santiago Soriano Romero |
| 2010/0222700 A1 | 9/2010 | Hibner |
| 2011/0124961 A1 | 5/2011 | Zimmon |
| 2011/0237975 A1 | 9/2011 | Secrest |

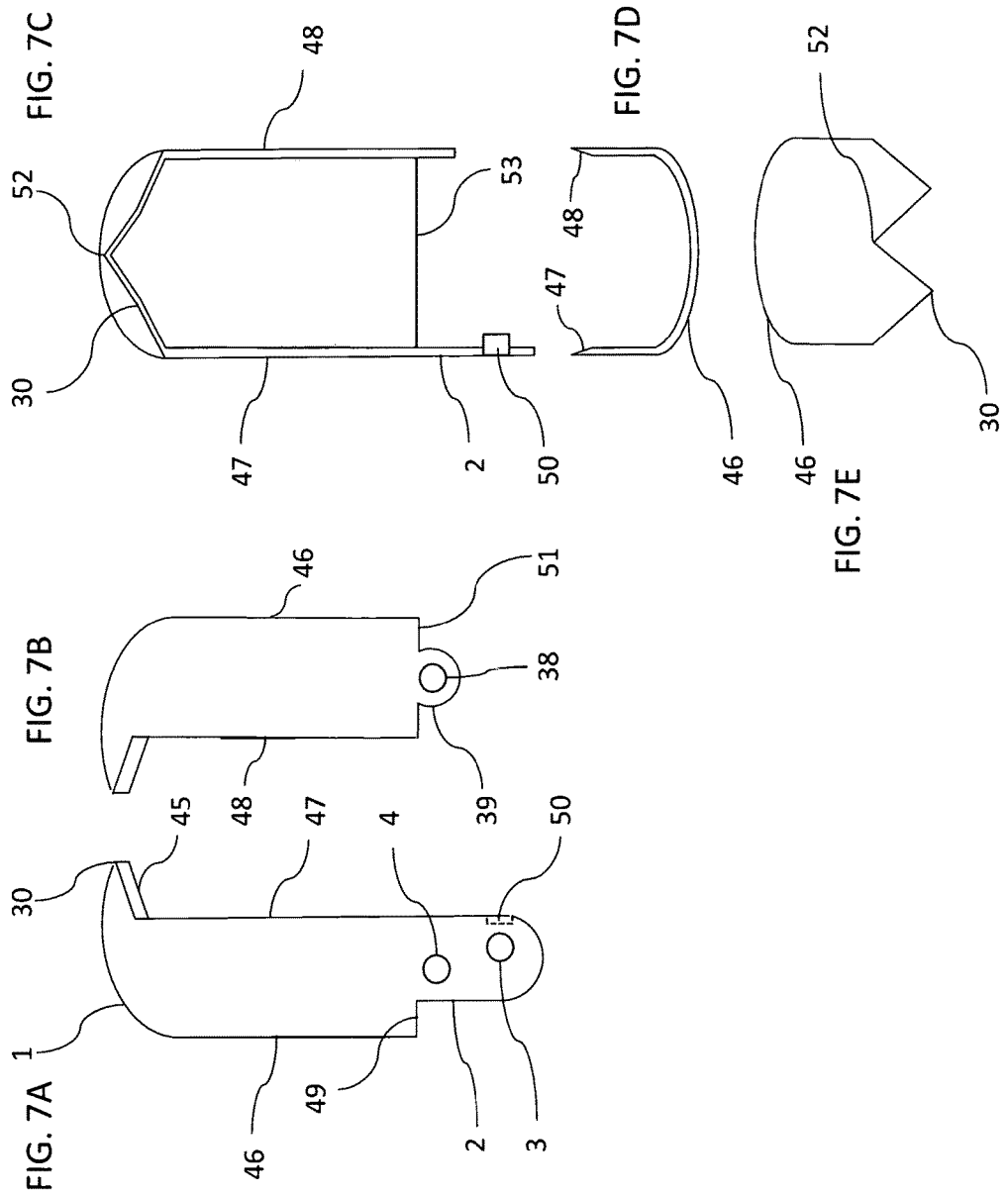

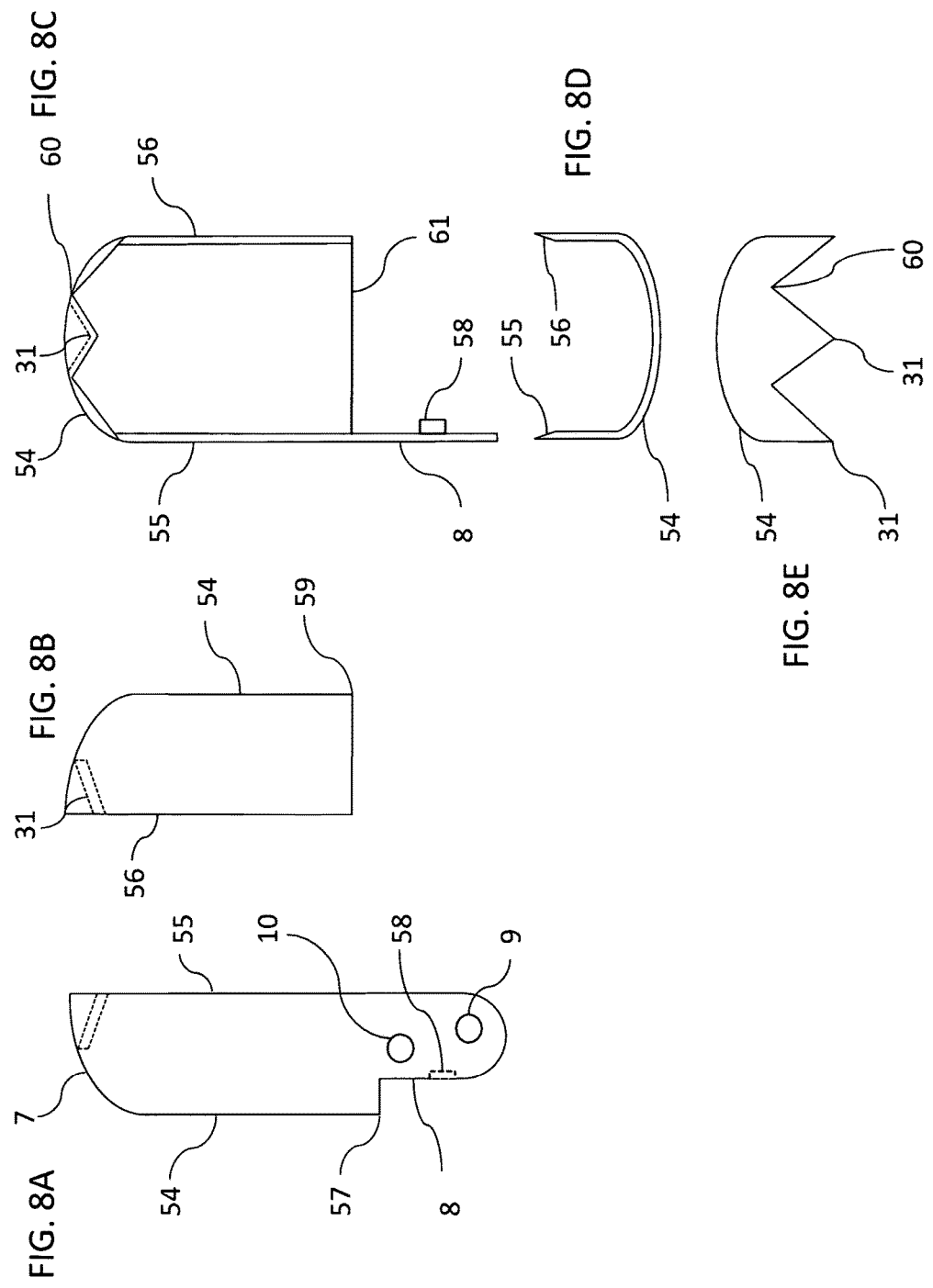

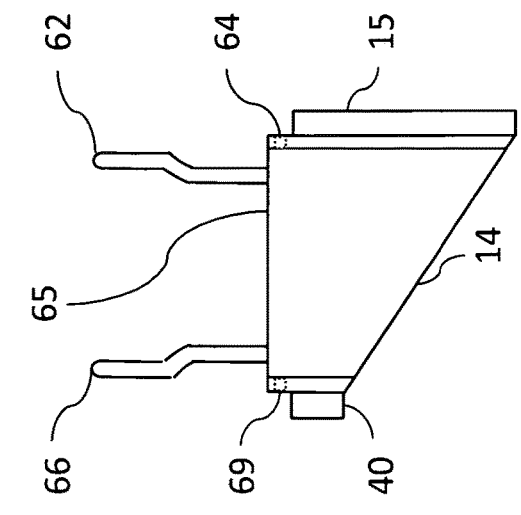
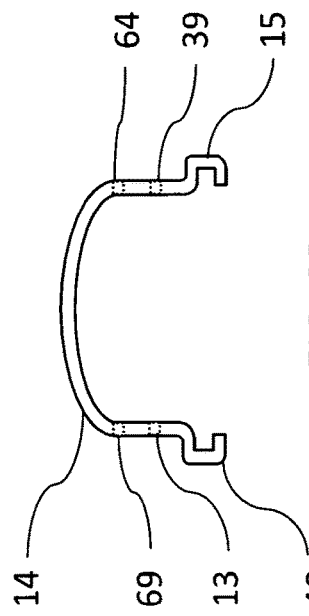
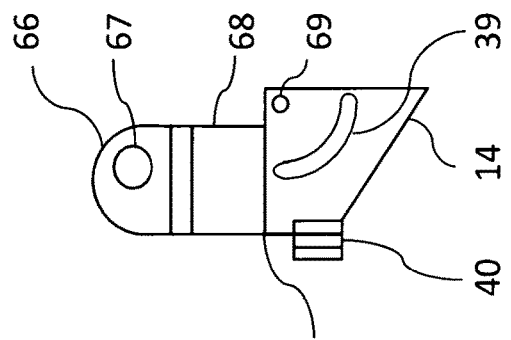
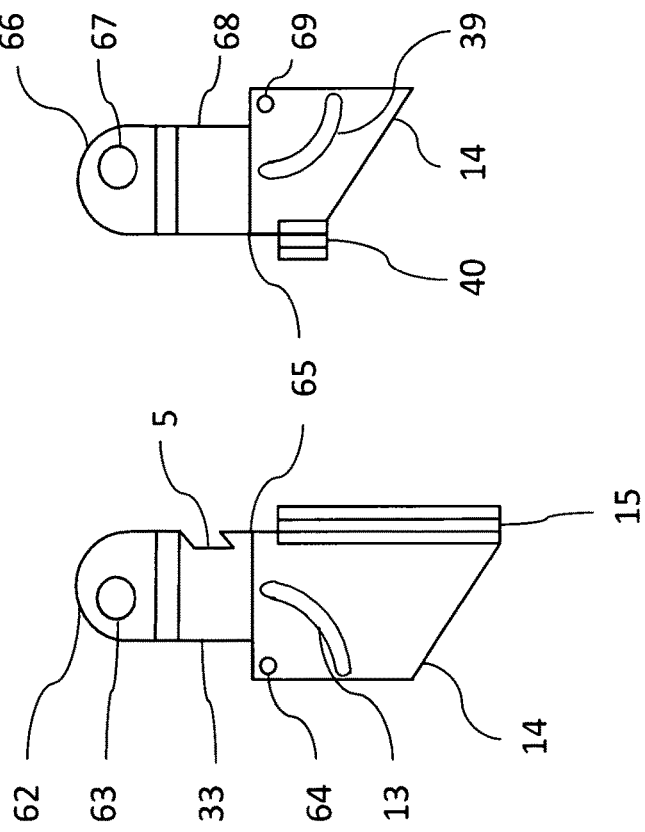

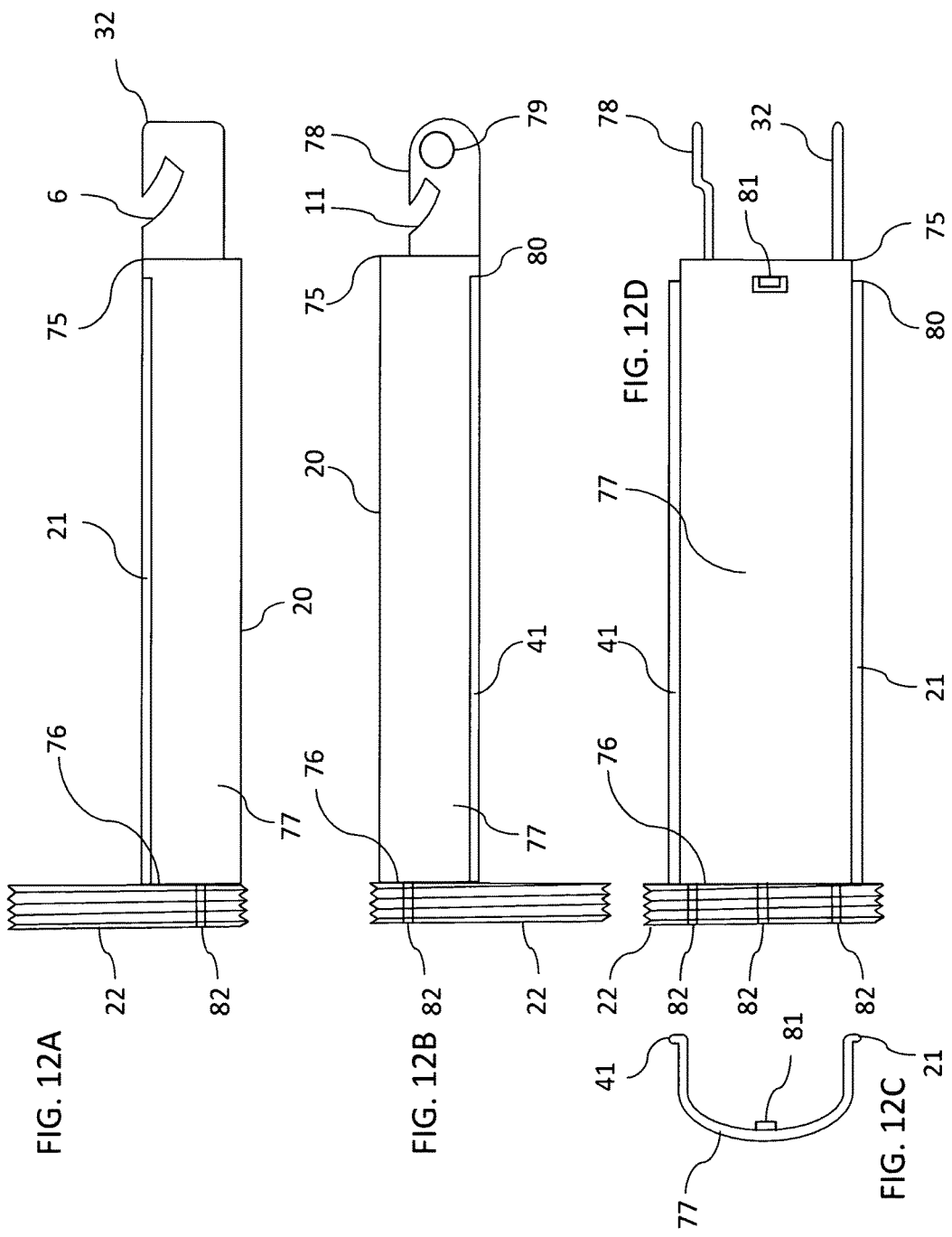

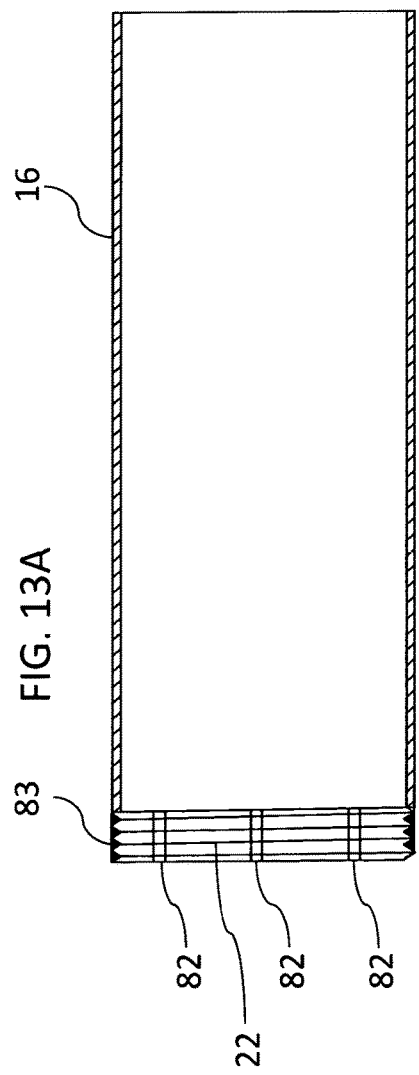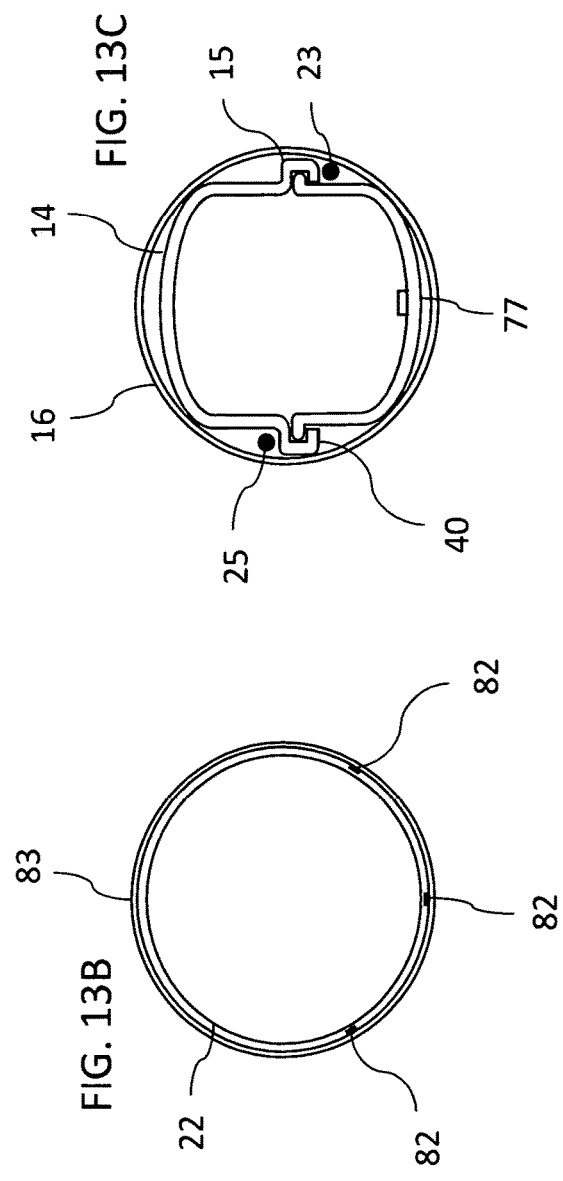

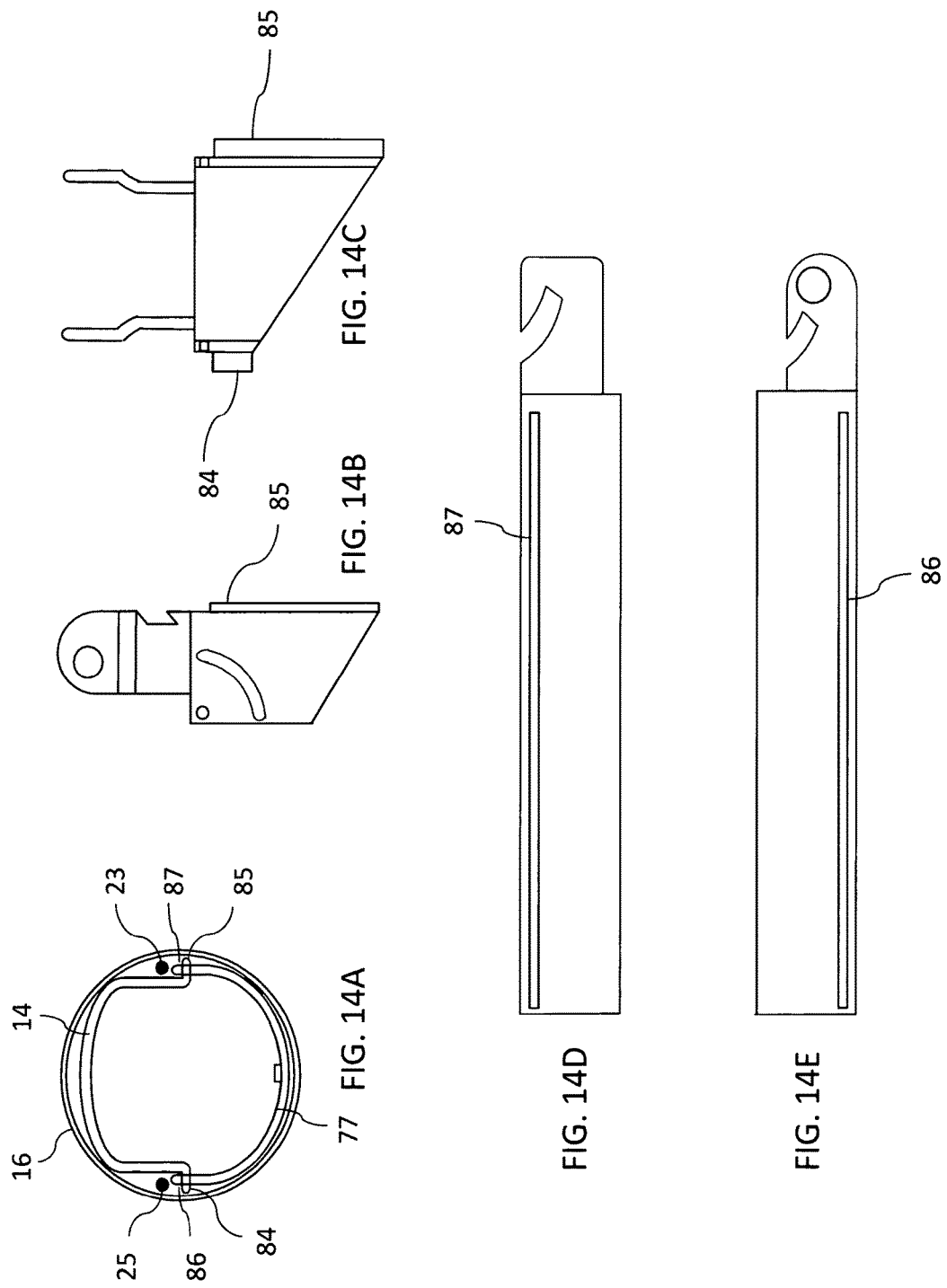

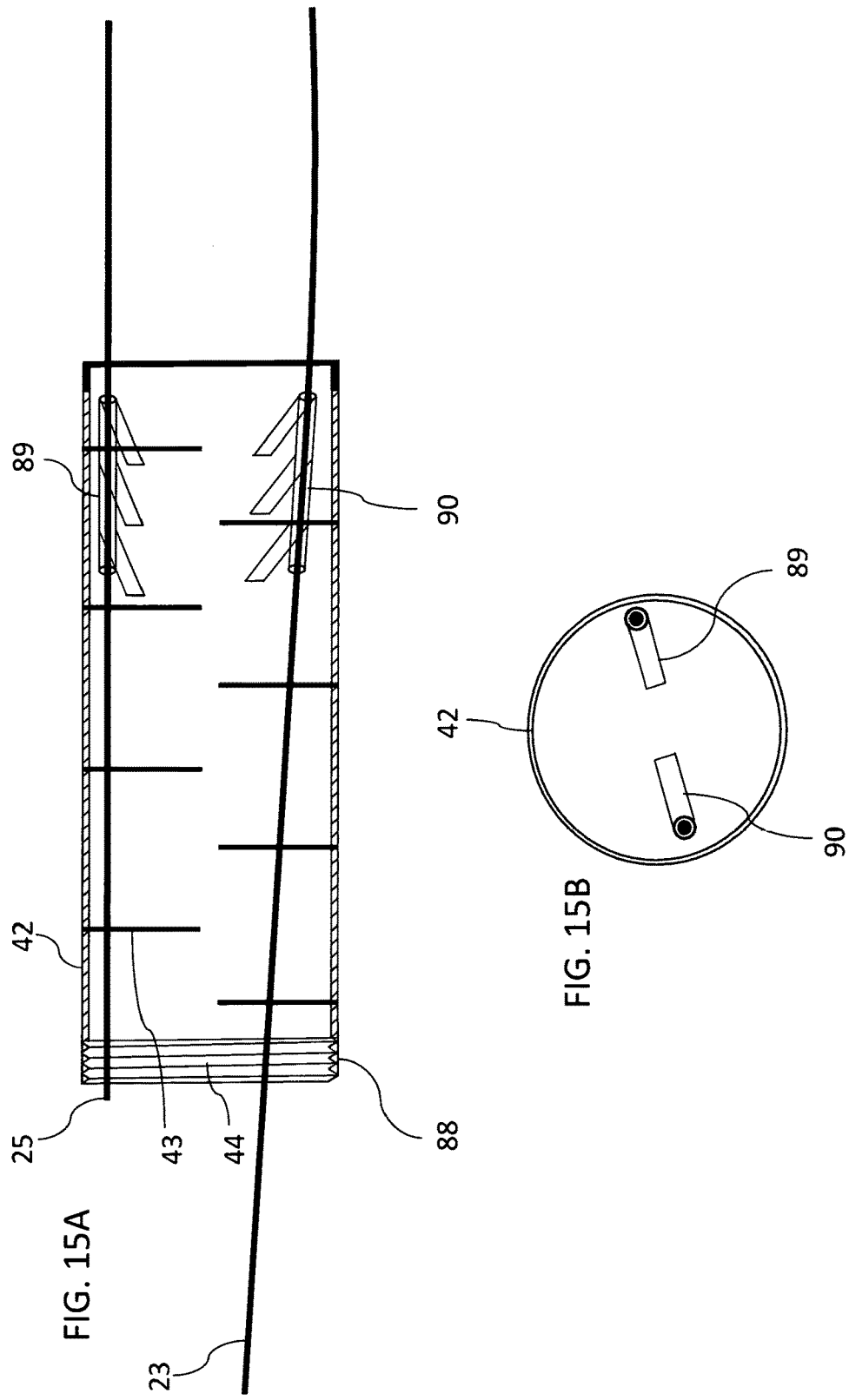

TISSUE SAMPLING DEVICE

CROSS REFERENCE TO RELATED APPLICATIONS

Attached please refer to the Information Disclosure Statement for the cross reference to related applications.

STATEMENT REGARDING FEDERALLY SPONSORED RESEARCH OR DEVELOPMENT

The present invention is not a federally sponsored research or development.

TECHNICAL FIELD

This invention relates to obtaining multiple tissue samples from a tubular or cavitary space of a body.

BACKGROUND OF THE INVENTION

Tissue biopsy through endoscope or laparoscope requires delivery of a biopsy instrument into a target area, acquiring a sample of tissue by cutting motion of the instrument and retrieval of said sample through said endoscope or laparoscope. The instruments are shaped in general as forward biting and cutting biopsy forceps at distal end, which are connected to a proximal knob via flexible wires. Since size of available biopsy forceps is small and each biopsy sample has to be retrieved separately one at a time, biopsy by endoscopic or laparoscopic forceps requires significant time and increases sampling error.

To circumvent these issues, there have been several devices proposed to collect multiple samples in one insertion of the biopsy forceps without the need to retrieve the forceps each time the sample was obtained.

The U.S. Pat. Nos. 5,746,216 and 6,019,758 describe methods of a multiple sample bioptome by axially linear movement of an outer tube over cutting jaws. Issues of said device include no actual mechanism of transport of procured samples to a sample storage space; narrower diameter of the sample storage space than that of the cutting jaws in closed position, thereby impeding transfer of the procured sample into the storage space.

The U.S. Pat. No. 5,762,069 uses a wire spiral axially located inside a flexible tube of biopsy forceps, which can be rotated to proximally move tissue samples inside the tube as a means for obtaining multiple samples. One drawback of the device is that rotational torque of the spiral needs to be significant enough to transfer samples that are viscous and tend to adhere to inner wall of the device. Another problem is that rotation of the spiral should be axially centered in the tube, which is hard to achieve with only one end of the spiral attached to a proximal end of the device.

The U.S. Pat. No. 5,779,648 proposes dual action mechanism of one of cutting members with rotary motion to cut tissue samples followed by axial motion to transfer said sample into a proximally located sample storage space. Issues of the device include slippery bite of tissue sample for cutting by the cutting unit due to premature transition of rotary biting force to axial motion before completion of cutting; limited axial motion of the cutting unit not adequate enough to push back said samples into the sample storage space; no mechanism to retrieve procured samples from the storage space.

The U.S. Pat. No. 5,782,747 proposes methods of procuring multiple tissue samples by using spring jaws to cut samples from tissue. One major problem is that the proposed mechanism requires tearing-off of tissue for procuring sample without cutting action of the jaws, which in practice would hardly achieve samples of adequate size for assessment. Furthermore the device does not have means to retrieve procured samples.

The U.S. Pat. Nos. 6,053,877, 6,110,127 and 6,632,182 describe methods of obtaining tissue samples serially into an axially longitudinal sample tube located proximally to cutting jaws that are slidably connected to a mid part of a multi-layered biopsy tube. Cutting action to procure tissue samples is achieved by axially linear movement of said layer of the tube. Said tissue samples are then sequentially to be stored by stuffing action of a new tissue sample upon the previously procured and stored samples. Issues of the devices include proximal transmission of distally forward force to move the mid layer upon contact with a target tissue, which may buckle the proximal portion of flexible wire of the biopsy instrument instead of exerting distally forward movement, resulting in inadequate cutting actions; presence of sticky friction between inner wall of the tube and the tissue samples, generating resistance to stuffing action of the newly procured sample; a need to maintain axially straight tubular structure of the tissue sample storage for a certain length to transmit distally forward force for cutting action and to allow proximally linear movement of the samples by backward stuffing action. The U.S. Pat. No. 6,632,182 proposes use of suction to pull in procured samples. Quality of the samples may deteriorate since the samples must travel inside the entire length of the tube upon suction from the distal end of said device to a storage space.

The U.S. Pat. Nos. 6,071,248 and 6,322,522 describe methods of procuring multiple tissue samples by using suction of air or fluid in cavity from which said samples are to be taken. Issues of the inventions include inadequate cutting force of the cutting jaws; adherence of said samples to the cutting jaws resulting in incomplete detachment of the samples from the cutting jaws; inadequate and uncertain mechanism of suction/aspiration to serially stock samples into the sample storage space, with the first stored sample blocking off the suction/aspiration conduit thereby prohibiting further storage of additional samples.

The U.S. Pat. No. 6,083,150 illustrates methods of procuring multiple biopsy samples by installing a sample storage space open to a proximal end of jaws. One drawback of the device is that there is no actual mechanism to proximally transport the samples from the jaws to the storage space other than serially stacking up samples proximally into an opening to the storage space.

The U.S. Pat. No. 6,139,508 uses sequential collections of tissue samples that are to be stored proximally through a sample guide arm. Axially linear transfer of samples to a proximal end is either unassisted or assisted by an auger inside a tube located at a distal end. One method of collecting multiple samples by the proposed device requires adequate forward pressure of the sample guide arm against tissue, which is supposed to proximally push back previously obtained samples stacked in the sample tube. The other method using the auger requires axial rotation of said auger to retrieve samples. Practical problems related to these methods include the forward pressure applied to the sample guide arm pushing the target tissue away from the cutting jaws due to elastic nature of the tissue and lack of adequate transport mechanism of procured samples proximally along the axis inside the sample tube. Furthermore, there is no firm stationary hold on the sample skewered in the auger when said auger rotates. Consequently the sample skewered in the auger may rotate together with the auger and may never move proximally in the sample tube.

The U.S. Pat. Nos. 5,562,102, 5,823,971, 5,840,044, 6,142,957 and 6,419,640 use a skewer in the middle of cutting jaws, which is to pierce a target tissue and pull the tissue into said cutting jaws for cutting. The cut tissue sample then is proximally stacked up along the skewer by subsequently obtained samples. Issues of these devices include poor quality of the samples that are pierced in the middle; inability to retrieve the samples unless the skewer is either completely pulled out from a distal end of the device or the samples are cut off further damaging the quality of the samples; a potential risk of perforation of thin wall of the gut. The U.S. Pat. No. 5,823,971 also proposes use of a cutting sling to cut samples off as an example of procuring samples. Problem of this proposal is that the sling should be both flexible and sharp enough to pull in and cut off samples. This requirement may result in premature material breakage of the sling.

The U.S. Pat. Nos. 5,810,744, 5,961,534 and 6,530,891 describe methods of procuring multiple samples by side cutting action. Issues of these devices include a need to position a distal end of said devices in parallel with a target tissue while maintaining the distal end linearly straight for a certain length to effect cutting actions. The U.S. Pat. No. 5,810,744 has no actual transport mechanism for procured samples to a proximal area of a storage space. The U.S. Pat. No. 5,961,534 proposes use of a wire sling as indexer that can be moved back and forth in front of the procured samples and use of index points that radially extend from an inner wall of said device, which is to capture said samples in the storage space. One issue of the index points is difficulties in manufacturing said points as part of the inner wall. The U.S. Pat. No. 6,530,891 may not have adequate cutting torque of the helical cutting blade since rotational torque must travel a long distance from the proximal end of said device to the distal end.

The U.S. Pat. No. 7,278,971 proposes use of a rack-pinion device located at a distal end of biopsy forceps, for transporting serial samples into storage space. One critical issue is that circular movement of the rack-pinion device located at right angle to the linear axis of said biopsy forceps significantly reduces size of the samples that could be practically transported.

The U.S. Pat. No. 7,794,409 uses a multi-chambered cutting device removably attached to a distal end of endoscope for cutting off and suctioning up tissue samples via a channel in the endoscope to store the samples. One caveat of the device is a need to establish and to maintain negative pressure in the cutting device, which requires tight fitting between the device and the target area. It potentially increases chances of bleeding from the target tissue into a space between the tissue and the device. Another issue is damage to samples during transit along a certain length of the channel of the endoscope.

The U.S. Pat. No. 7,846,107 describes methods of collecting multiple samples into a sample storage space connected to an endoscopic instrument. Samples are to be obtained by conventional biopsy forceps, which then are to be transported through a channel in a tubular shaft of the endoscope by vacuum suction. Said methods require unobstructed transport of the samples in the channel upon vacuum suction through the length of the tubular shaft of the endoscope. One issue of the patent is that vacuum suction may damage samples adversely in a way accurate pathologic interpretations of the samples may be affected.

These aforementioned patents proposed devices and methods, which are limited with inadequate or damageable samples, or with complicated mechanistic actions. Consequently there practically has not been a widespread use of these devices for multiple sampling of tissue. Successful devices and methods require procured samples of good quality and of adequate size for pathologic evaluation; easy operability with conventional endoscopic instruments; consistent operation with minimal variation of operability and of quality of samples upon a range of varied target tissues.

SUMMARY OF THE INVENTION

The present invention describes a biopsy device and methods for collecting multiple samples in one introduction into a tubular or cavitary structure of a living body without a need to retrieve the device each time a sample is obtained. A linearly tubular device comprises a distal end, a proximal end and a tubular shaft connecting both said distal and proximal ends. At the distal end, the device comprises a tissue cutting assembly comprising a pair of differentially pullable clamshell cups with cutting jaws, a sample transport assembly comprising a sample transport unit, a sample chamber and a pair of differential pull wires, and a sample storage assembly comprising a plurality of sample storage housings. Both said sample transport unit and sample chamber have distal arms to which the differentially pullable clamshell cups are connected via shanks. An axially tubular housing encloses the sample transport unit and the sample chamber and is releasably connected proximally to the tubular shaft via an internal helical fastener. The pair of differential pull wires are connected to a control knob at the proximal end and distally to the shanks of the differentially pullable clamshell cups. Said pull wires provide the differentially pullable clamshell cups with rotation and the sample transport unit with linear movement.

In one embodiment, at the distal end, two opposing pair of semi-cylindrical differentially pullable clamshell cups with distally located tissue cutting jaws are connected proximally to shanks and open proximally to the sample transport unit. One of the shanks of each cup has two apertures, with a distal aperture connected via a rotatable pin to a distal arm of said sample transport unit and a proximal aperture located proximally from said distal aperture. Each pull wire is attached to the proximal aperture and rotates the shank about the rotatable pin of the distal aperture.

In another embodiment, a part of an axial border of one of the pair of shanks in between of the distal and proximal apertures has a securing tab that slides in a curvilinear slot bordered by a notch located at one of the distal arms of the sample transport unit and by an open slot in an opposing distal arm of the sample chamber. Said open slot becomes a closed slot by said notch once the pair of the differentially pullable clamshell cups close tight, aligning the pins and the cup shanks along the longitudinal axis of the device. On rotation of the shank connected to the sample transport unit, said shank is guided by the securing tab inside the closed slot to a predefined range of rotation. The securing tab prevents premature linear movement of said shank in a proximal direction before said securing tab moves out completely from the open slot of the sample chamber.

In one embodiment, the sample transport unit comprises a semi-cylindrical body with a pair of slidable guiders located on both sides of said body, which are C-shaped longitudinal grooves with the open part of C facing the axial center of said body. Corresponding to the guiders of C-shaped groove, the sample chamber has a pair of rails made of right-angled bending of both longitudinal borders of said sample chamber. Each said rail is slidably encased by the C-shaped groove and said guiders of C-shaped groove slide axially on said rails, thus providing linear movement of the sample transport unit on the semi-cylindrical tubular sample chamber. In another embodiment, a longitudinal slot is located along each axial border of said sample chamber, in which a corresponding rail protruding from each axial border of the sample transport unit slides, providing linear movement of said sample transport unit along the axis.

In a preferred embodiment, one of the pair of shanks of the differentially pullable clamshell cup is attached via the pin to one of the distal arms of the sample transport unit. Axial movement, in a proximal direction, of the pull wire attached to the shank is translated to pivotal movement of said shank until said shank is aligned along the longitudinal axis and both differentially pullable clamshell cups close tightly. Once said shank is aligned longitudinally, the securing tab of said shank reversibly locks in the notch of said distal arm, thereby making both said shank and said distal arm become a single moving unit longitudinally along the axis. Further axial movement of said pull wire in a proximal direction moves said single moving unit proximally on the sample chamber, with said sample transport unit pulling said differentially pullable clamshell cup into the sample housing. The sequence of pivotal movement followed by axial movement of said differentially pullable clamshell cup proximally allows stockpiling of procured samples into said sample housing.

In one embodiment, there is provided a reversibly detachable sample catcher inserted in the sample chamber. The sample catcher captures samples in said sample chamber by radially projected flexible ribbons angled toward the proximal end, which are made of thin sheet metal or elastic polymers. The sample catcher is detachable from the inner wall of the sample chamber and is to hold procured samples in said sample chamber, preventing them from being pulled back distally to the differentially pullable clamshell cups.

In one embodiment, the sample transport unit has a disc located at right angle at the distal end of the body of said sample transport unit, which proximally pushes previously stored samples in the sample chamber when said sample transport unit moves proximally toward the proximal end of the sample housing. Said disc is lifted up close to the inner wall of the upper part of said sample transport unit in pivotal movement when it moves back out distally toward the distal end of said sample chamber, thereby bypassing said stored samples.

In one embodiment, the disc is an extension of central part of the distal end of the sample transport unit and collapses only in proximal direction. In another embodiment, the disc has two sets of paired pivotal projections, with one pair on the top of both vertical sides of said disc and the other pair below the top pivotal projections on both sides. Each of the top projections serves as pivot and is inserted in an aperture located on the top of the side wall of the body of the sample transport unit. Each of the two lower projections is inserted in a curvilinear slot on each side wall of the sample transport unit and moves along the curvilinear slot, with said top projection being the center of curvilinear movement of said lower projection.

In another embodiment, an tubular extension sample housing is releasably inserted in between of the sample housing and the tubular shaft. The extension housing is attached to the tubular shaft via an internal helical fastener. The extension housing accommodates multiple samples that are transported proximally by the sample transport unit. The extension housing is made of thin sheet metal or polymers, and has multiple short-length slits located at right angle to the longitudinal axis of said extension housing, each slit spaced apart in a way said slits provide multi-directional flexible bending of the extension housing.

In one embodiment, a pair of pull wires from the control knob of the proximal end of the device are attached distally to the apertures of the shanks and provide both pivotal movement of the differentially pullable clamshell cups and axial movement of the sample transport unit. One of the differentially pullable clamshell cups connected to the sample transport unit is attached at its shank to a linear pull wire without coil configuration. The other differentially pullable clamshell cup is attached to a second pull wire of the pair, which has a coiled portion of extension-coil type for a certain length between its attachment to the proximal knob and its attachment to the shank connected to the distal arm of the sample chamber. The coil shaped portion of said pull wire winds around said linear pull wire and is configured to accommodate differences in length of the two pull wires when said pull wires are pulled proximally by the proximal knob of the device. The linear pull wire attached to the shank that is connected to the sample transport unit moves axially for longer distance than the other coiled pull wire attached to the shank that is connected to the stationary sample chamber, to carry said sample transport unit along the length of said sample chamber. The coiled pull wire stretches its coiled portion for the length of said sample chamber.

In one embodiment, one piece of tissue sample is obtained by traditional cutting action of the cutting jaws of the differentially pullable clamshell cup and then is transported by said differentially pullable clamshell cup into the sample chamber to be stored. Once the sample is stored, said sample is secured by the sample catcher while said differentially pullable clamshell cup moves distally for subsequent cutting actions. When the second sample is transported into said sample chamber, the first sample in said chamber is pushed proximally by the sample collecting disc of the sample transport unit, thereby leaving behind a space for the second sample to be stored. This sequence of actions continues until adequate number of samples is obtained. The stored samples are released by rotating off the sample housing from the internal helical fastener.

BRIEF DESCRIPTION OF THE DRAWINGS

FIG. 7 shows a schematic view of an example of individual parts of the differentially pullable clamshell cup that is to get connected to the sample transport unit and is to be pulled into the sample housing.

FIG. 8 shows a schematic view of an example of individual parts of the differentially pullable clamshell cup that is to get connected to the distal arm of the stationary sample chamber and is to have pivotal movement.

FIG. 9 shows a schematic view of an example of individual parts of the sample transport unit.

FIG. 12 shows a schematic view of an example of the sample chamber.

FIG. 13 shows a schematic view of an example of the sample housing (FIG. 13A & FIG. 13B) and a schematic cross-sectional view of an example of said sample housing with both the sample transport unit and the sample chamber in place (FIG. 13C).

FIG. 14 shows a schematic view of another example of both the sample transport unit and the sample chamber in a different configuration.

FIG. 15 shows a schematic view of an example of the tubular extension sample housing, with the pull wires running through said housing.

DETAILED DESCRIPTION OF THE DRAWINGS

As described below, the present invention provides a device in a number of configurations and methods of use. It is to be understood that the descriptions are solely for the purposes of illustrating the present invention, and should not be understood in any way as restrictive or limited. Embodiments of the present invention are preferably depicted with reference to FIGS. 1 to 16, however, such reference is not intended to limit the present invention in any manner. The drawings do not represent actual dimension of devices, but illustrate the principles of the present invention.

Figure 1:
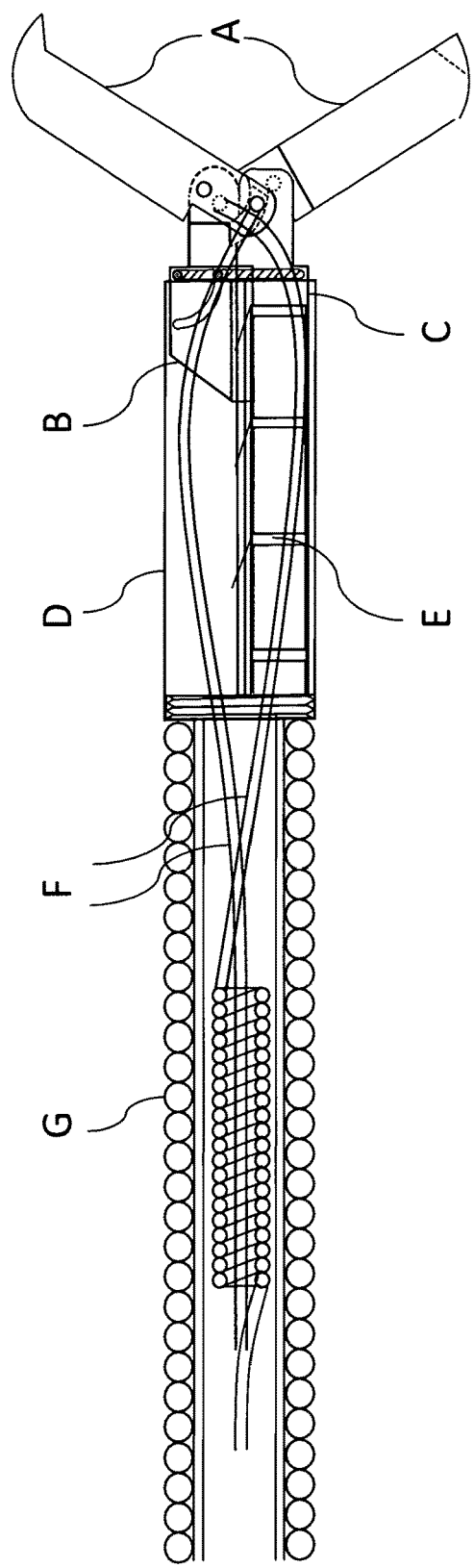
FIG. 1 shows a schematic explanatory profile view of the present invention.

FIG. 1 illustrates a schematic profile view of an example of a tissue sampling device comprising a tissue cutting assembly, a sample transport assembly and a sample storage assembly. The tissue cutting assembly comprises a pair of differentially pullable clamshell cups A connected via corresponding shanks to both distal arms of a sample transport unit B and of a sample chamber C. The sample transport assembly comprises the sample transport unit B, the sample chamber C and a pair of differential pull wires F. The sample storage assembly comprises a sample housing D that encloses both B and C and a sample catcher E releasably inserted in said sample chamber C. The pair of differential pull wires F are connected distally to corresponding apertures of said shanks and proximally to a knob located at the proximal end of said device. A flexible tubular shaft G is connected distally to said sample housing D via an internal helical fastener and proximally to said proximal end of said device.

In one embodiment, the differential pull wires advance distally along the axis of the device to open the differentially pullable clamshell cups by pivotal movement at said shanks to capture a target tissue. Once said target tissue is captured by said differentially pullable clamshell cups, said differentially pullable clamshell cups close tight by reverse pivotal movement to cut off said target tissue from the target area. Once both the differentially pullable clamshell cups are aligned longitudinally along the axis of said device, one of said differentially pullable clamshell cups connected to the sample transport unit is pulled proximally, together with the target sample inside said cup and with said sample transport unit longitudinally along the axis in a proximal direction, which stores said target sample inside said sample chamber. Said differentially pullable clamshell cup that was pulled back proximally is released distally together with said sample transport unit by returning said pull wire in a distal direction. Said tissue sample that was captured by said sample catcher does not move with said differentially pullable clamshell cup as it is held by said sample catcher inside said sample chamber.

Figure 2:
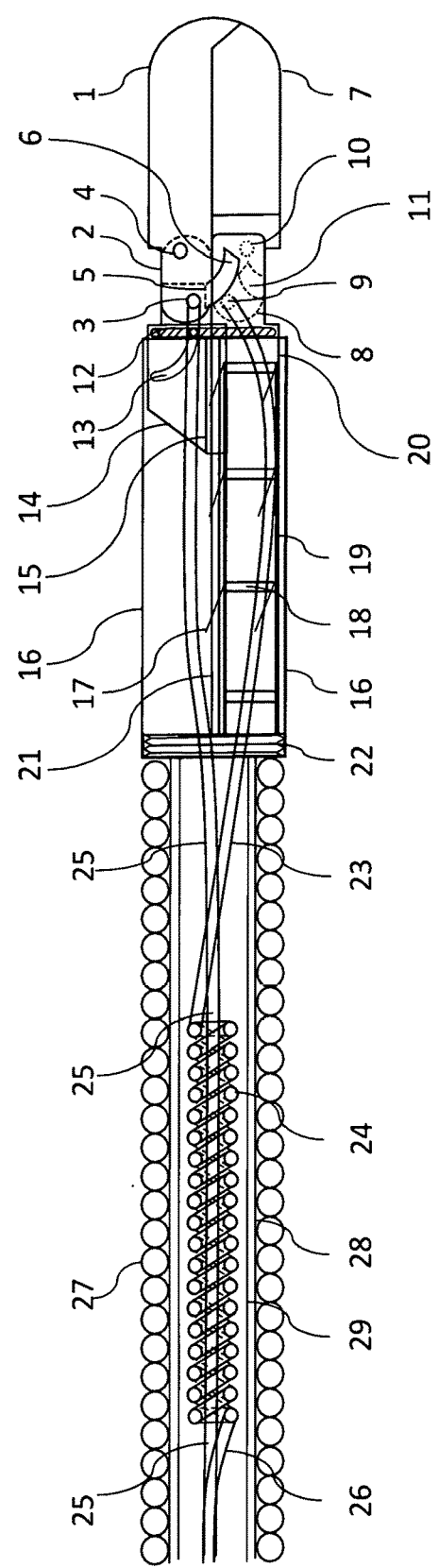
FIG. 2 shows itemized components of FIG. 1, with both the differentially pullable clamshell cups in a closed position.

Referring to FIG. 1, FIG. 2 depicts individual components of the schematic overview in profile of the device of the present invention in a neutral, closed position. Layout of differentially pullable clamshell cups and shanks is illustrated in 1 through 11. Differentially pullable clamshell cup 1 is connected to shank 2 that has two apertures 3 and 4. The aperture 3 is connected with pull wire 25 that provides pivotal movement of the shank 2 about the aperture 4. In one embodiment, a securing tab on one edge of the shank 2 releasably slides in notch 5 of a distal arm of sample transport unit 14 when the differentially pullable clamshell cup 1 is aligned longitudinally with the axis of said device and is to slide in curvilinear slot 6 located at one side of a distal arm of sample chamber 20 in a pivotal movement about the aperture 4 when the differentially pullable clamshell cup 1 opens. Outline of indented notch 5 follows the curvilinear outline of the slot 6 to form a closed slot in a closed position of the differentially pullable clamshell cups, in and out of which the securing tab of the shank 2 slides.

Differentially pullable clamshell cup 7 is connected to shank 8 that is the only shank of the cup 7 and has two apertures 9 and 10. The aperture 9 is connected with pull wire 23 that provides pivotal movement of the shank 8 about the aperture 10. The differentially pullable clamshell cup 7 does not linearly move into the sample chamber 20 but provides pivotal movement about the aperture 10. In one embodiment, one edge of the shank 8 has a securing tab that releasably slides in curvilinear slot 9 of the other side of a distal arm of said sample chamber 20 in a pivotal movement about the aperture 10 when the differentially pullable clamshell cup 7 opens.

In one embodiment, the sample transport unit B comprises asymmetric semi-cylindrical body 14, two slidable guiders located longitudinally along both sides of said body, a pair of distally protruding arms located on both sides of the axis and sample collecting disc 12 located at right angle to the axis of the distal end of said body. The body 14 has a pair of identical curvilinear slots located on both sides of said body and a pair of oppositely placed apertures located close to the distal end of said body. In FIG. 2, one of the two said slidable guiders is illustrated as 15 and one curvilinear slot as 13. Detailed illustrations of the sample transport unit are provided in FIG. 9.

The sample chamber C is semi-cylindrical tube with its rectangular side being open to sample housing 16. A pair of rails are located at both axially longitudinal edges of said rectangular side, which is made of right-angled bending of the axial edges of said chamber. One of said rails is illustrated as 21 and a wall of the chamber as 20. The slidable guider 15 encases said rail 21 longitudinally and slides on said rail 21 linearly along the axis. Inside the sample chamber C, there is provided the sample catcher E that comprises longitudinal spines 19, connecting ribbons 18 and sample catching leaves 17. The sample catcher E is releasably inserted into said sample chamber and captures samples by narrow-angled, linear leaves that are unidirectional toward the proximal end of said device.

The sample housing D encloses the sample transport unit B, the sample chamber C and the sample catcher E, and is releasably connected to the flexible tubular shaft G via internal helical fastener 22. Wall of the sample housing is designated as 16. Procured tissue samples are stored in the sample housing that can be released from the helical fastener by axial rotation of said housing.

The flexible tubular shaft G comprises wound wire 27, inner layers 28 and 29. The wire 27 encircles differential pull wires F in a helical fashion along the axis from the distal end to the proximal end of said device and provides said shaft with longitudinal flexibility and circumferential rigidity. The distal end of said flexible shaft is immovably connected to the internal helical fastener 22 of the sample chamber C and provides said internal helical fastener with structural support. Said wound wire 27 is separated from the differential pull wires F by the inner layers 28 and 29 along the length of said flexible shaft, which prevents friction between said wound wires and said differential pull wires and provides unimpeded lengthening and shortening of a segment of expansion coil 24 of the differential pull wire 23.

Differential pull wires 23 and 25 are connected distally to the apertures 9 and 3, respectively. The wire 25 runs straight from the distal connection to the proximal knob of said device. From the distal end, the wire 23 runs straight proximally to the coiled segment 24 that is of expansion coil type. Said coiled segment then becomes straight wire 26 proximally that is connected to the proximal knob of said device. The wire 25 provides pivotal movement of the differentially pullable clamshell cup 1 about the aperture 4 and moves the sample transport unit B and the differentially pullable clamshell cup 1 longitudinally along the axis between the proximal and distal end of the sample chamber. Linear distance displacement of said wire 25 is greater by the length of said sample chamber than that of said wire 23 that only needs to provide pivotal movement of the differentially pullable clamshell cup 7 about the aperture 10. When both said wires 25 and 26 are pulled proximally together by the proximal knob of said device, difference in the linear displacement between said wires 25 and 23 is compensated by lengthening of said coiled segment 24 of said wire 23. Said coiled segment 24 concentrically encircles said wire 25 and narrowed diameter of said coil by lengthening is larger than the diameter of said wire 25.

Figure 3:
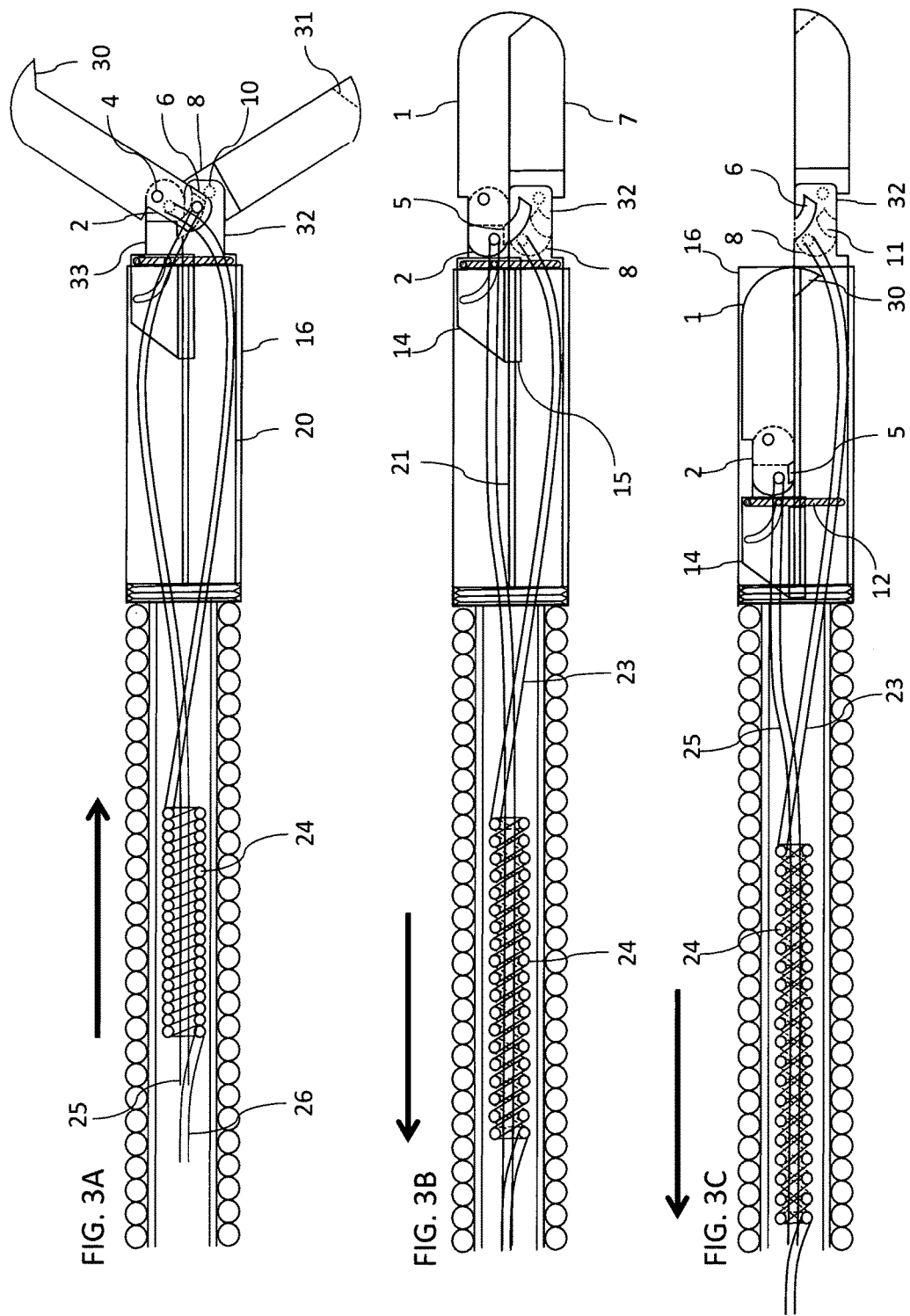
FIG. 3 illustrates a schematic view of an example of sequential actions of the device, with the differentially pullable clamshell cups in an open position (FIG. 3A) and in a closed position (FIG. 3B), and with one of said cups proximally retracted into the sample housing (FIG. 3C).

FIG. 3 illustrates opening (FIG. 3A) and closing (FIG. 3B) of the differentially pullable clamshell cups and proximal retraction (FIG. 3C) of one differentially pullable clamshell cup into the sample housing in sequence. The sample catcher E is not depicted for simplicity of illustration. In FIG. 3A, the pull wires 26 and 25 are pushed distally by the proximal knob, compressing the coiled segment 24 and advancing both pull wires 25 and 23 distally. Distal movement of both pull wires 25 and 23 generates pivotal movement of the shanks 2 and 8, respectively about the apertures 4 and 10, thereby opening the differentially pullable clamshell cups in preparation for capturing a target tissue.

Capturing of tissue is facilitated by interlocking jaw teeth 30 and 31 of said differentially pullable clamshell cups. The shank 2 is connected to distal arm 33 of the sample transport unit via the aperture 4. Said securing tab of one edge of said shank 2 slides in the slot 6 located in distal arm 32 of the sample chamber.

In FIG. 3B, said proximal knob pulls both pull wires 25 and 26 proximally, which translates into closing of the differentially pullable clamshell cups by reverse pivotal movement of the shanks 2 and 8. Said securing tab of said shank 2 has slid out from the slot 6 to the notch 5 of the distal arm 33. Once both differentially pullable clamshell cups are aligned longitudinally with the axis of said device and said securing tab of said shank 2 is completely out from said slot 6, the differentially pullable clamshell cup 1 is releasably locked in the distal arm 33 by insertion of said securing tab of the shank 2 into the notch 5. With this movement, the differentially pullable clamshell cup 1 is longitudinally aligned with the sample transport unit B and can be pulled by said sample transport unit B linearly along the axis into the sample housing D.

In FIG. 3C, further proximal pulling of said pull wires results in linear proximal movement of the sample transport unit B along the rail 21 of the sample chamber 20, guided by the sample guider 15 to the end of the internal helical fastener 22. With this movement, the differentially pullable clamshell cup 1 is pulled into the sample housing D. With the proximal pulling of pull wires, the coiled segment 24 of the pull wire 23 is lengthened for the longitudinal length of the sample chamber C beyond the distance for pivotal movement of the shank 8, which enables said proximal knob to pull both pull wires simultaneously for the same length.

Figure 4:
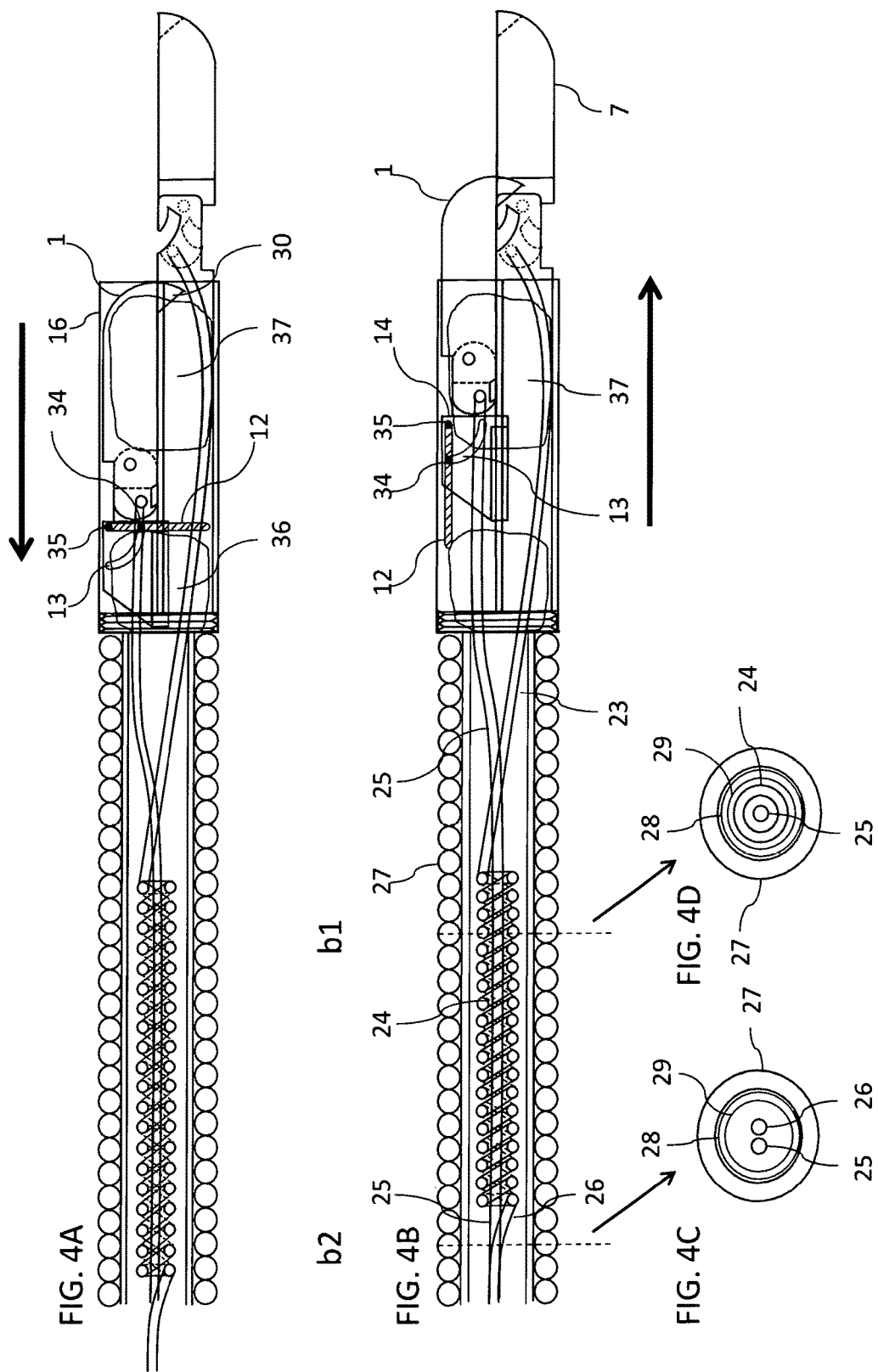
FIG. 4 shows a schematic view of an example of sequential sample collecting actions of the sample collecting disc attached to the distal end of the body of the sample transport unit (FIG. 4A & FIG. 4B), and a schematic cross-sectional view of the differential pull wire portion of said device (FIG. 4C).

FIG. 4A and FIG. 4B illustrate a schematic example of profile view of proximal stacking of procured tissue samples 36 and 37 in the sample housing D by directional movements of the sample collecting disc 12. FIG. 4C shows cross-sectional views of the differential pull wires F. For simplicity of illustration, the sample catcher E is not depicted in FIG. 4. In one embodiment, the sample collecting disc 12 is attached at right angle to the distal end of the body 14 of the sample transport unit B via pivots 34 and 35. The pivot 34 is inserted in the curvilinear slot 13 located on the side of the body 14 and the pivot 35 is inserted in a corresponding aperture.

The first sample 36 that was stored before the second sample 37 is pushed back proximally toward the end of the internal helical fastener 22 by the sample collecting disc 12 placed at right angle in front of the sample 36 while the second sample 37 is brought into the sample housing D by the differentially pullable clamshell cup 1. The sample collecting disc 12 is passively lifted up to the inner wall of the sample housing wall 16, guided by the pivot 34 in the curvilinear slot 13, when the differentially pullable clamshell cup 1 moves out distally after having stacked the second sample 37 in the sample housing D. This stacking process repeats until the sample housing is full of stored samples.

FIG. 4C depicts an example of a configuration of the differential pull wires F. At cross-section b1, the coiled segment 24 of the pull wire that is connected to the differentially pullable clamshell cup 7 via the pull wire 23 forms concentric coil of expansion-coil type for some length inside the outer wall complex of the wound wire 27 and the inner layers of 28-29. The pull wire 25 that is connected to the differentially pullable clamshell cup 1 runs straight through in the center of the coiled segment 24. At cross-section b2, the coiled segment 24 becomes straight pull wire 26 that runs in parallel with the pull wire 25 in a proximal direction to get connected to the proximal knob of said device.

Figure 5:
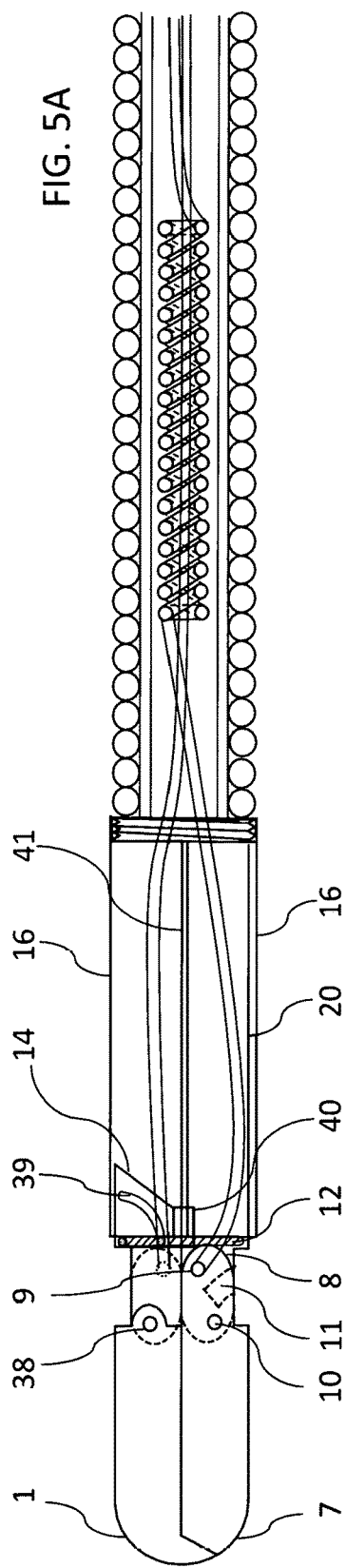
FIG. 5 shows a schematic profile view of an example of the opposite side of the device.

FIG. 5 illustrates an example of an opposite view of the distal end of said device, showing the other part of paired components. For simplicity of illustration, the sample catcher E is not depicted in FIG. 5. Aperture 38 corresponds to the aperture 4 of the differentially pullable clamshell cup 1. Curvilinear slot 39 corresponds to the slot 13. Sample guider 40 corresponds to the sample guider 15. Rail 41 corresponds to the rail 21. In one embodiment, the body 14 of the sample transport unit B is configured asymmetrically to evenly distribute friction between the sample guiders and the rails on both sides of the sample chamber C when the differentially pullable clamshell cup 1 and the sample transport unit B are pulled longitudinally by the pull wire 25 on one of both sides of said cup.

Figure 6:
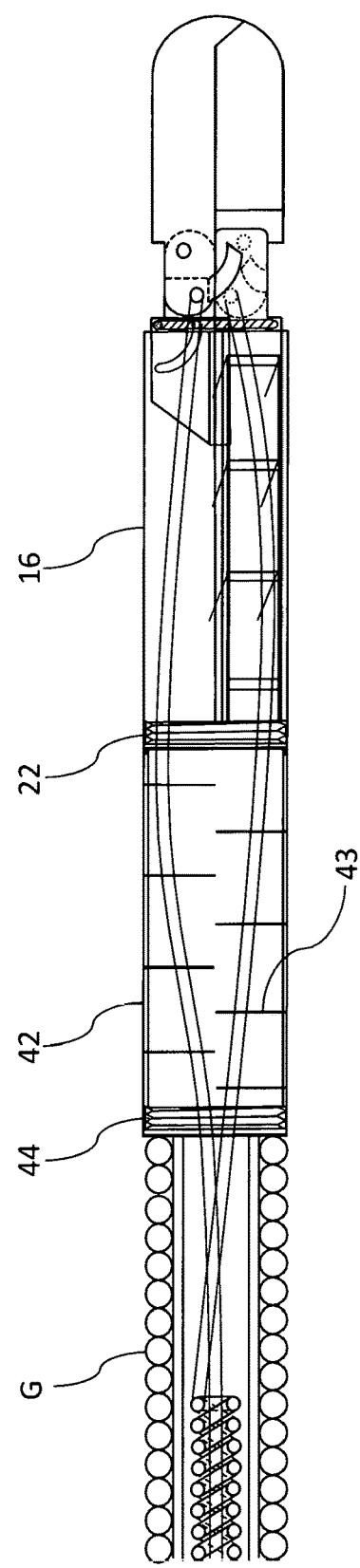
FIG. 6 shows a schematic view of an example of the tubular extension sample housing attached to the proximal end of the sample housing.

FIG. 6 depicts an example of the tubular extension sample housing 42 releasably attached distally to the internal helical fastener 22 of the sample housing D and proximally to internal helical fastener 44 that is immovably connected to the flexible tubular shaft G. Said tubular extension sample housing 42 is fenestrated by a plurality of slits 43 made at right angle to the axis of said housing 42, to provide flexibility of said housing and to prevent pressure inside said housing from building up by serially stacking up sticky samples in the space of said housing. Main purpose of said extension sample housing is to provide storage space for additional samples.

FIG. 7 illustrates an example of the differentially pullable clamshell cup 1 connected to the shank 2. FIG. 7A and FIG. 7B show a profile view, FIG. 7C a front view, FIG. 7D a cross-sectional view and FIG. 7E a top-down view of said cup. The differentially pullable clamshell cup 1 has two jaw teeth 30 that are to be interlocked with jaw teeth of the clamshell 7. At the tip portion of the differentially pullable clamshell cup, there are provided two teeth 30 and one pointed groove 52 in between of the two teeth. Main function of the jaw teeth is to retract a procured sample inside said differentially pullable clamshell cup proximally toward the sample chamber. Said tip portion merges with the body of said cup, bordered by 46 and 47 on one side and 46 and 48 by the other side. Said body proximally is bordered by cut-out section 49 on one side, before said body joins the shank 2. The other side view of the body shows cut-out border 51, corresponding to 49. The cut-out border 49 and 51 are connected with each other by proximal border 53 of said body. The shank 2 has two apertures 3 and 4. The distal aperture 4 anchors the shank 2 to one of distal arms of the sample transport unit B by a pin that provides rotation. The proximal aperture 3 is connected with the pull wire 25 that provides pivotal movement of the shank 2 about the aperture 4 and linear displacement of the shank 2 longitudinally along the axis. On the inner edge of the shank 2, there is provided securing tab 50 that is releasably inserted into the notch 5 and the slot 6 of FIG. 2. In FIG. 7B, aperture 38 surrounded by rim 39 is shown, corresponding to the aperture 4, which is connected to the other distal arm of the sample transport unit B by a pin that provides rotation. Edges 45, 47 and 48 are sharpened to cut tissues by slicing action.

FIG. 8 depicts an example of the differentially pullable clamshell cup 7 connected to the shank 8. FIG. 8A and FIG. 8B show a profile view, FIG. 8C a front view, FIG. 8D a cross-sectional view and FIG. 8E a top-down view of said cup. Corresponding to the jaw teeth 30 and the pointed groove 52 of the differentially pullable clamshell cup 1, the differentially pullable clamshell cup 7 has three interlockable jaw teeth 31 and two pointed grooves 60 in between of the three teeth. Main function of the jaw teeth of the differentially pullable clamshell cup 7 is to provide structural support of the jaw teeth 30 of the differentially pullable clamshell cup 1. Body of the differentially pullable clamshell cup 7 is bordered by 54 and 55 on one side and 54 and 56 on the other side. Said body proximally is bordered by cut-out section 57 before joining the shank 8 on one side. The other side of the differentially pullable clamshell cup 7 ends at border 59 without shank. The cut-out section 57 and the border 59 are connected with each other by proximal border 61 of said body. The shank 8 has two apertures 9 and 10. The distal aperture 10 anchors the shank 8 to one of distal arms of the sample chamber C by a pin that provides rotation, which is the only attachment to said sample chamber C. The proximal aperture 9 is connected with the pull wire 23 that provides pivotal movement of the shank 8 about the aperture 10. On the inner edge of the shank 8, there is provided securing tab 58 that is releasably inserted into the slot 11 of FIG. 5. Edges 31, 55 and 56 are sharpened to cut tissues by slicing action.

Figure 10A:
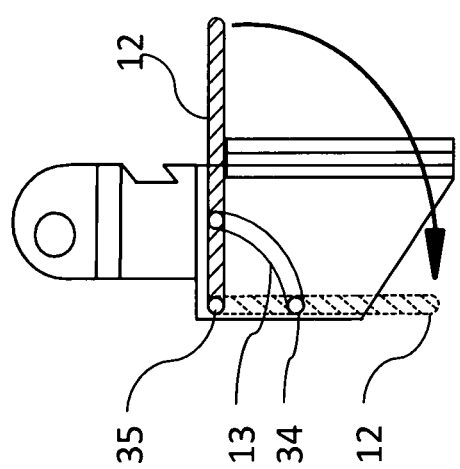
FIG. 10 shows a schematic view of an example of the sample collecting disc, with its pivots inserted into corresponding apertures of the body of the sample transport unit.

FIG. 9 shows an example of the sample transport unit B that comprises a pair of distal arms 62 and 66 connected proximally to the main body 14 and a pair of guiders 15 and 40 longitudinally running on both sides of the body 14. FIG. 9A and FIG. 9B show a profile view, FIG. 9C a top-down view and FIG. 9D a cross-sectional view at the level of the distal end of the body 14. In FIG. 9A, the distal arm 62 has aperture 63 that is connected to said distal aperture 4 of FIG. 7A by said rotatable pin. Said distal arm 62 is connected to the distal end 65 of the body 14 by the shank 33 that has the indented notch 5. Said notch 5 covers an open end of the curvilinear slot 6 to form a closed slot when the sample transport unit B is distally advanced to the distal end of said device. The securing tab 50 of FIG. 7 releasably slides in and out of said notch 5 in pivotal movement about the aperture 63. In FIG. 9B, the distal arm 66 is connected to said distal end 65 of the body 14 by shank 68 and has aperture 67 that is connected to said distal aperture 38 of FIG. 7A by said rotatable pin. Said body 14 has a pair of symmetrically located apertures 64 and 69 and a pair of symmetrically located curvilinear slots 13 and 39. A pair of corresponding pins 35 and 70 of the sample collecting disc 12 illustrated in FIG. 10 are inserted in the apertures 64 and 69 and provide pivotal movement of said sample collecting disc. Referring to FIG. 10, said pivotal movement of the sample collecting disc 12 is rotatably guided by another set of pins 34 and 71 of said disc 12 inserted in said curvilinear slots 13 and 39. In FIG. 9C and FIG. 9D, said body 14 has a pair of guiders 15 and 40 located on both sides of said body, which are C-shaped grooves with the open part of C facing the axial center of said body. Said C-shaped guiders slide longitudinally along the axis on the rails 21 of FIGS. 3B and 41 of FIG. 5A.

Figure 10B:
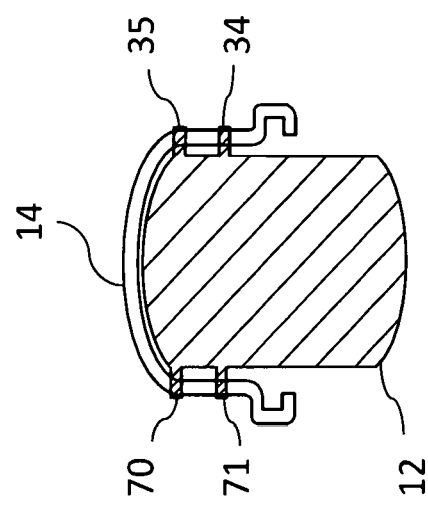
Figure 10C:
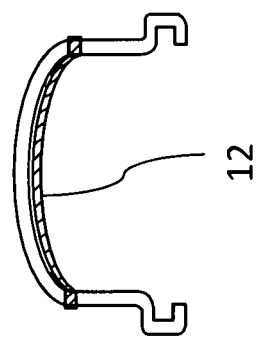
Figure 11C:
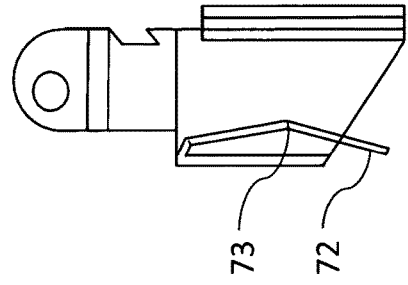
FIG. 11 shows a schematic view of another example of the sample collecting disc that is an extension of the body of the sample transport unit.
Figure 11F:
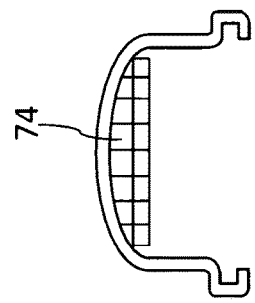
Figure 11B:
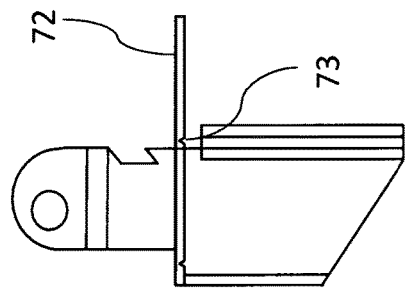
Figure 11E:
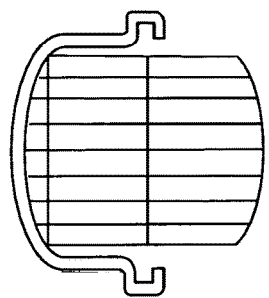
Figure 11A:
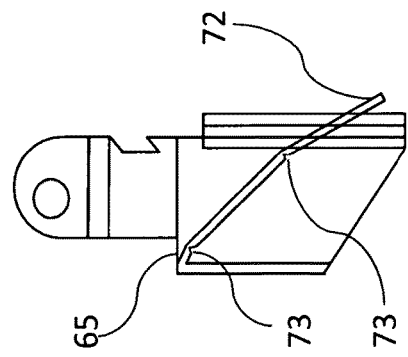
Figure 11D:
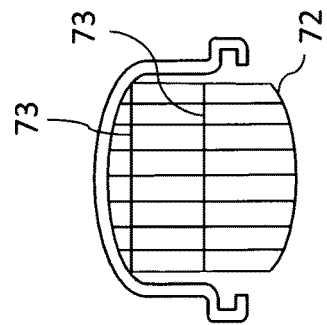

FIG. 10 illustrates proximally directional pivoting movement of the sample collecting disc 12 about pins 35 and 70. Referring to FIG. 4A, FIG. 10B depicts a cross-sectional view of said disc 12 located at right angle to the longitudinal axis of the body 14, covering the majority of the cross-sectional area of the sample housing D. Referring to FIG. 4B, said disc 12 is lifted up to the uppermost inner wall of said body 14 to reduce its cross-sectional area to minimum, shown in FIG. 10C.

In another embodiment, shown in FIG. 11, sample collecting disc 72 is a part of the body 14, extending from the distal end 65 of the body 14. Said disc 72 has a plurality of horizontal nicks 73 on its proximal surface, which only bend reversibly in proximal direction. FIG. 11A shows a neutral position of said disc 72, FIG. 11B an extended position at right angle to the body 14 and FIG. 11C a collapsed position to the uppermost inner wall of the body 14. Referring to FIG. 4A, the extended position of the disc 72 in FIG. 11B is to push previously stored tissue sample(s) proximally when the sample transport unit B is pulled proximally. When said sample transport unit B moves distally toward the distal end of the sample housing D as in FIG. 4B, said disc 72 passively collapses at said nicks 73 shown in FIG. 11C, resulting in a minimum cross-sectional area 74. FIG. 11D, FIG. 11E and FIG. 11F show cross-sectional views of said disc 72 in each position.

FIG. 12 illustrates an example of the sample chamber C that is semi-cylindrical tube with its longitudinal rectangular side open to the sample housing D. FIG. 12A and FIG. 12B show a profile view, FIG. 12C a cross-sectional view and FIG. 12D a top-down view. Semi-cylindrical main body 77 is connected at its distal end 75 to a pair of distal arms 32 and 78 and immovably at its proximal end 76 to the internal helical fastener 22. On both sides of the body 77, there are a pair of the rails 21 and 41 that are connected at right angle to said body 77 and run longitudinally from distal end 80 of said rails to proximal end 76. Close to the distal end 75 of the body 77, there is provided securing clip 81 located centrally in the body 77 for the sample catcher E to be releasably inserted. The distal arm 78 has aperture 79 that is connected by a rotatable pin to the aperture 10 of the shank 8 and the curvilinear slot 11 in and out of which the securing tab 58 of the shank 8 slides, shown in FIG. 8. A proximal part of the distal arm 78 is slightly depressed inward to accommodate attachment of the pull wire 23 to the aperture 9 of the shank 8 shown in FIG. 3. The distal arm 32 has the curvilinear slot 6 in and out of which the securing tab 50 of the shank 2 slides, depicted in FIG. 7. The internal helical fastener 22 is fenestrated by linear holes, shown as 82, longitudinally along the axis of said device, through which proximal prongs of the sample catcher E are releasably insertable and lockable by directional rotation of the sample housing D.

FIG. 13 depicts an example of the hollow tubular sample housing D that comprises the wall 16 of the tubular portion and helically threaded portion 83 rotationally inserted over the internal helical fastener 22 of the sample chamber C. FIG. 13A shows a profile view, FIG. 13B a cross-sectional view at the level of the helically threaded portion 83 and FIG. 13C a cross-sectional view at the tubular portion 16 with both the sample transport unit B and sample chamber C in place. In the space between of the outer wall 16 and both the sample transport unit B and sample chamber C, the pull wires 23 and 25 run longitudinally along the axis of said device.

FIG. 14 illustrates another embodiment of the sample transport unit B and the sample chamber C. FIG. 14A shows a cross-sectional view of both the sample transport unit and sample chamber inside the tubular wall 16 of the sample housing D, FIG. 14B a profile view of the sample transport unit B, FIG. 14C a top-down view of the said transport unit, FIG. 14D and FIG. 14E a profile view of said sample chamber C. Said sample transport unit comprises two linear rails 84 and 85 protruding at right angle from both the longitudinal borders of the body 14. Said sample chamber has two longitudinally placed linear slots 86 and 87 along the upper borders of said chamber, one on each side of the chamber. Said rails 84 and 85 of said sample transport unit slide longitudinally in the corresponding slots 86 and 87 of said chamber.

FIG. 15 depicts an example of the hollow tubular extension sample housing that comprises the wall 42 of the tubular portion and helically threaded portion 88 corresponding to the internal helical fastener 44. FIG. 15A shows a profile view and FIG. 15B shows a cross-sectional view at the tubular portion. Said tubular extension sample housing 42 is fenestrated by a plurality of slits 43 made at right angle to the axis of said housing 42. In one embodiment, the pull wires 23 and 25 have tubular sample catchers 89 and 90 for some length, which are immovably inserted over the pull wires inside said extension sample housing. The tubular sample catchers 89 and 90 have a plurality of proximally angled flexible leaves that project toward the center of the tubular extension housing. Said angled leaves are pulled toward the proximal end of said device when the pull wires 23 and 25 are pulled proximally, thereby assisting proximal stacking movement of procured samples in said extension sample housing. When said pull wires move distally, said leaves collapse in a way they do not move stored samples distally.

Figure 16B:
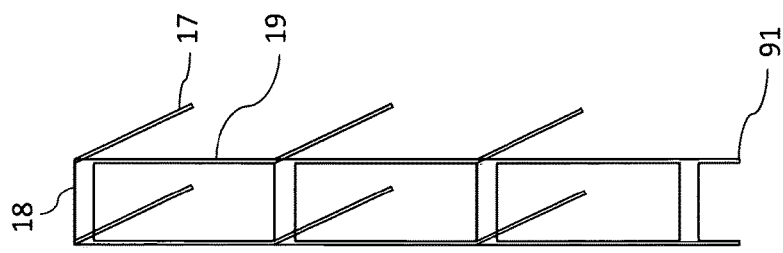
FIG. 16 shows a schematic view of an example of the sample catcher that is releasably insertable in the sample chamber.
Figure 16A:
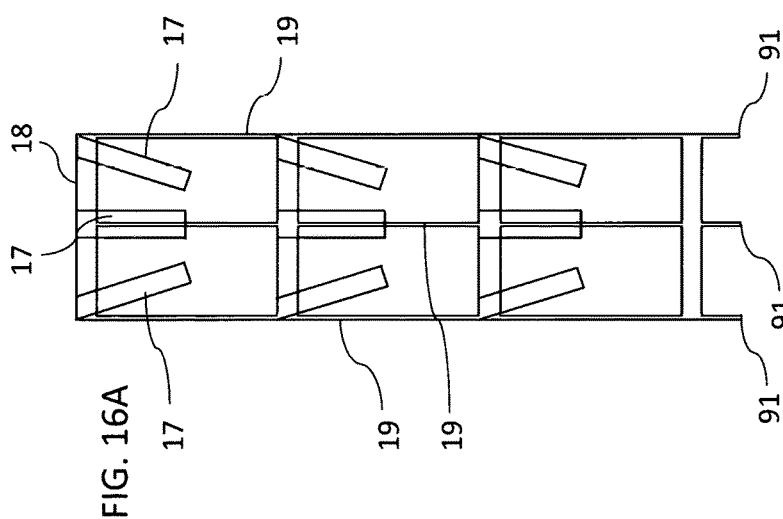
Figure 16C:
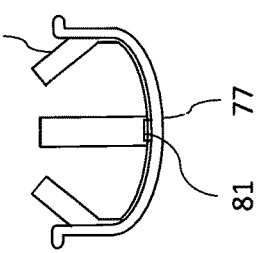

FIG. 16 illustrates an example of the sample catcher E that is releasably insertable to the inner wall of the sample chamber C. FIG. 16A shows a top-down view, FIG. 16B a profile view and FIG. 16C a cross-sectional view of the sample catcher placed in the sample chamber body 77. The sample catcher comprises the longitudinal spines 19, the connecting ribbons 18 and the sample catching leaves 17. The sample catcher is secured by releasable locking of the prongs 91 inserted in the holes 82 of the internal helical fastener 22, and by the securing clip 81 that holds the distal end of the top ribbon 17 onto the inner wall 16 of the sample housing. Said sample catcher captures tissue samples by narrow-angled leaves that are unidirectional toward the proximal end of said device. Said catching leaves are flexible to some extent, but they maintain proximally directed orientation.

It is to be understood that the aforementioned description of the device and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A tissue sampling device comprising: a proximal end, a distal end, and a flexible tubular shaft connecting said proximal end with said distal end, a longitudinally linear mechanical device having a tissue cutting assembly, a sample transport assembly, and a sample storage assembly arranged in tandem at the distal end, wherein the distal end of the tissue sampling device is configured to be introduced through an endoscope, wherein the tissue cutting assembly is configured to removably obtain serial tissue samples from an endoscopic target area, wherein the sample transport assembly is configured to transport the serial tissue samples to the sample storage assembly, wherein the tissue cutting assembly comprises a first and second differentially pullable clamshell cups, and wherein the first differentially pullable clamshell cup is configured to be anchored to a first differential pull wire, and the second differentially pullable clamshell cup is configured to be anchored to a second differential pull wire, the first and second differentially pull wires being enclosably housed at a distal portion of the flexible tubular shaft, wherein, the sample transport assembly comprising a sample transport unit in a semi-cylindrical tubular configuration and a stationary sample chamber in a semi-cylindrical tubular configuration, wherein the sample transport unit is configured to be slidably assembled with the stationary sample chamber, wherein the sample transport unit is configured to slidably move on the stationary sample chamber along a longitudinal axis of the stationary sample chamber, and wherein the stationary sample chamber is configured to enclosably store the serial tissue samples;

wherein the first differentially pullable clamshell cup has a first pivoting center thereof at a proximal arm of the first differentially pullable clamshell cup, wherein a second differentially pullable clamshell cup has a second pivoting center thereof at a proximal arm of the second differentially pullable clamshell cup, wherein the first differentially pullable clamshell cup is aligned in parallel with the second differentially pullable clamshell cup along a longitudinal axis of the first and second differentially pullable clamshell cups, wherein the proximal arm of the first differentially pullable clamshell cup is pivotably connected to a distal arm of the stationary sample chamber at the first pivoting center, and wherein the proximal arm of the second differentially pullable clamshell cup is pivotably connected to a distal arm of the sample transport unit at the second pivoting center; and the sample storage assembly comprising a tubular sample housing and a sample catcher, wherein the sample catcher comprises a plurality of needle-shaped leaves angled toward the proximal end of the tissue sampling device, wherein the sample catcher is configured to be fastenably disposed inside the stationary sample chamber of said sample transport assembly, and wherein the sample catcher is configured to capture the serial tissue samples.

2. The tissue sampling device according to claim 1,
wherein the first pivoting center for the first differentially pullable clamshell cup is disposed at the distal arm of the stationary sample chamber;
wherein the second pivoting center for the second differentially pullable clamshell cup is disposed at the distal arm of the sample transport unit;
wherein the first pivoting center and the second pivoting center are aligned by a distance on a circumferential axis of the first and second differentially pullable clamshell cups;
wherein the distal arm of the stationary sample chamber comprises a first curvilinear slot configured to mate with a protruding tab disposed at the proximal arm of the first differentially pullable clamshell cup so as to guide pivoting movement of the first differentially pullable clamshell cup about the first pivoting center; and
wherein the distal arm of the stationary sample chamber comprises a second curvilinear slot configured to mate with a protruding tab disposed thereof at the proximal arm of the second differentially pullable clamshell cup so as to guide pivoting movement of the second differentially pullable clamshell cup about the second pivoting center.

3. The tissue sampling device according to claim 2, wherein
the protruding tab disposed at the proximal arm of the second differentially pullable clamshell cup is configured to pivotably slide out of the second curvilinear slot of the distal arm of the stationary sample chamber, and to slide in a notch of the distal arm of the sample transport unit following the longitudinal alignment of the second differentially pullable clamshell cup with the longitudinal axis of the first differentially pullable clamshell cup so as to fully close the first and second differential pullable clamshell cups, and wherein a sliding-out movement of the protruding tab from the second curvilinear slot of the distal arm of the stationary sample chamber is configured to allow the second differentially pullable clamshell cup to be pulled toward the proximal end of the tissue sampling device.

4. The tissue sampling device according to claim 2, wherein
a notch of the distal arm of the sample transport unit is provided on an edge of the distal arm of the sample transport unit in alignment with the second curvilinear slot of the distal arm of the stationary sample chamber, wherein the notch is configured to engage with the protruding tab of the second differentially pullable clamshell cup, wherein a full engagement of the notch with the protruding tab aligns the sample transport unit longitudinally with the second differentially pullable clamshell cup, and wherein a longitudinal alignment of the sample transport unit with the second differentially pullable clamshell cup is configured to allow a longitudinal movement of the sample transport unit together with the second differentially pullable clamshell cup along the longitudinal axis of the stationary sample chamber.

5. The tissue sampling device according to claim 1, wherein the sample transport unit further comprises:
a semi-cylindrical body, a pair of distal arms, a pair of longitudinal guiders, and a sample collecting disc;
the semi-cylindrical body is provided in a semi-cylindrical tubular configuration, wherein the semi-cylindrical body adjoins the pair of distal arms along a longitudinal axis of said semi-cylindrical body on each side of said semi-cylindrical body, wherein the semi-cylindrical body adjoins laterally the pair of longitudinal guiders on each side of the semi-cylindrical body, and wherein the semi-cylindrical body is configured to be pivotably coupled with the sample collecting disc disposed at a distal end of said semi-cylindrical body;
each one of the pair of distal arms is provided as a flat panel longitudinally adjoining the semi-cylindrical body, wherein each one of the pair of distal arms has an aperture at a distal end thereof, and wherein the aperture of each one of the pair of distal arms is configured to be coupled with the pivoting center of the second differentially pullable clamshell cup;
each one of the pair of longitudinal guiders is provided as a C-shaped longitudinal groove, wherein each one of the pair of longitudinal guiders comprises a depressed part of the C-shaped longitudinal groove facing an axial center of the semi-cylindrical body, wherein each one of the pair of longitudinal guiders is configured to slide on a longitudinal rail disposed on a lateral edge of the stationary sample chamber; and
the sample collecting disc is provided as a flat panel pivotably inserted in the sample transport unit at a right angle to the longitudinal axis of the sample transport unit, wherein the sample collecting disc is configured to push the serial tissue samples inside the sample transport unit toward the proximal end of the tissue sampling device upon proximal movements of the sample transport unit.

6. The tissue sampling device according to claim 1, wherein the stationary sample chamber further comprises:

an open semi-cylindrical tube, a pair of distal arms, a pair of longitudinal rails, and an internal helical fastener;

wherein the open semi-cylindrical tube adjoins the pair of distal arms of the stationary sample chamber along a longitudinal axis of the open semi-cylindrical tube on each side of the open semi-cylindrical tube, wherein a lateral edge of the open semi-cylindrical tube adjoins the pair of longitudinal rails along the longitudinal axis of the open semi-cylindrical tube on each side of the open semi-cylindrical tube, wherein a proximal end of the open semi-cylindrical tube adjoins the internal helical fastener, and wherein the open semi-cylindrical tube is configured to store the serial tissue samples;

each one of the pair of distal arms is provided as a flat panel longitudinally adjoining the open semi-cylindrical tube, wherein each one of the pair of distal arms has an aperture at a distal end thereof, and wherein the aperture is configured to be coupled with the pivoting center of the first differentially pullable clamshell cup;

each one of the pair of longitudinal rails is provided as a male projection on a lateral edge of the open semi-cylindrical tube, wherein each one of the pair of longitudinal rails is configured to slidably mate with a longitudinal guider of the sample transport unit;

wherein the internal helical fastener is immovably attached to a distal end of the flexible tubular shaft, and wherein the internal helical fastener is configured to fastenably mate with a helically threaded portion of a tubular sample housing.

7. The tissue sampling device according to claim 6, wherein the tubular sample housing comprises:

a hollow tube, and a helically threaded portion;

wherein the hollow tube slidably encloses the sample transport assembly, a portion of the first and second differential pull wires and the sample catcher, and wherein the hollow tube is configured to store the serial tissue samples; and wherein the helically threaded portion is fixedly disposed at a distal end of the hollow tube, wherein the helically threaded portion is configured to rotatably fasten the tubular sampling housing to the internal helical fastener of the stationary sample chamber, and wherein the helically threaded portion is configured to rotatably unfasten the tubular sample housing from the internal helical fastener of the stationary sample chamber so as to unload the serial tissue samples.

8. A tissue sampling device comprising: a proximal end, a distal end, and a flexible tubular shaft connecting said proximal end with said distal end, a longitudinally linear mechanical device having a tissue cutting assembly, a sample transport assembly, and a sample storage assembly arranged in tandem at the distal end, wherein the distal end of the tissue sampling device is configured to be introduced through an endoscope, wherein the tissue cutting assembly is configured to removably obtain serial tissue samples from an endoscopic target area, wherein the sample transport assembly is configured to transport the serial tissue samples to the sample storage assembly, wherein the tissue cutting assembly comprises a first and second differentially pullable clamshell cups, and wherein the first differentially pullable clamshell cup is configured to be anchored to a first differential pull wire, and the second differentially pullable clamshell cup is configured to be anchored to a second differential pull wire, the first and second differentially pull wires being enclosably housed at a distal portion of the flexible tubular shaft, wherein, the first differential pull wire is provided with an expansion coil spring disposed at a distal end of the first differential pull wire, wherein the distal end of the first differential pull wire is configured to be anchored to a proximal arm of the first differentially pullable clamshell cup, wherein the distal end of the first differential pull wire is configured to pivot the first differentially pullable clamshell cup about a first pivoting center of the first differentially pullable clamshell cup, wherein the expansion coil spring is configured to coaxially encircle a distal portion of a second differential pull wire, and wherein the expansion coil spring is configured to be expanded over a distal portion of the second differential pull wire; wherein, the second differential pull wire is provided with a straight wire coaxially encircled by the expansion coil spring of the first differential pull wire, wherein the second differential pull wire comprises a straight wire disposed at a distal portion of the second differential pull wire, wherein a distal end of the second differential pull wire is configured to be anchored to a proximal arm of the second differentially pullable clamshell cup, wherein the distal end of the second differential pull wire is configured to pivot the second differentially pullable clamshell cup about a second pivoting center of the second differentially pullable clamshell cup, wherein the distal end of the second differential pull wire is configured to longitudinally pull the second differentially pullable clamshell cup for a length along a longitudinal axis of the flexible tubular shaft proximally into a stationary sample chamber following a longitudinal alignment of the second differentially pullable clamshell cup with a longitudinal axis of the first differentially pullable clamshell cup, and wherein a longitudinal pulling of the second differentially pullable cup by the second differential pull wire is configured to coincide with an expansion of the expansion spring of the first differential pull wire; and a polymeric layer is provided to coat an inner surface of the flexible tubular shaft and an inner surface of the expansion coil spring of the first differential pull wire, wherein the polymeric layer is configured to reduce friction around the expansion coil spring of the first differential pull wire.

\* \* \* \* \*